(12) United States Patent
Van Der Mark

(10) Patent No.: US 8,531,662 B2
(45) Date of Patent: Sep. 10, 2013

(54) METHOD AND DEVICE FOR OPTICALLY EXAMINING THE INTERIOR OF TURBID MEDIA

(75) Inventor: Martinus Bernardus Van Der Mark, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 283 days.

(21) Appl. No.: 12/997,627

(22) PCT Filed: Jun. 12, 2009

(86) PCT No.: PCT/IB2009/052512
§ 371 (c)(1),
(2), (4) Date: Dec. 13, 2010

(87) PCT Pub. No.: WO2009/153719
PCT Pub. Date: Dec. 23, 2009

(65) Prior Publication Data
US 2011/0090499 A1 Apr. 21, 2011

(30) Foreign Application Priority Data
Jun. 17, 2008 (EP) .................................. 08158407

(51) Int. Cl.
*G01J 3/28* (2006.01)
(52) U.S. Cl.
USPC ............................ 356/328; 356/319; 356/326
(58) Field of Classification Search
USPC .................. 356/326, 328, 317, 39, 300, 302, 356/305
See application file for complete search history.

(56) References Cited

U.S. PATENT DOCUMENTS

| 5,461,475 A | 10/1995 | Lerner et al. |
| 6,031,609 A | 2/2000 | Funk et al. |
| 6,399,935 B1 | 6/2002 | Jovin et al. |
| 7,151,601 B2* | 12/2006 | MacKinnon et al. .......... 356/326 |
| 7,221,452 B2* | 5/2007 | Berger et al. .................. 356/327 |
| 7,265,830 B2* | 9/2007 | Wang ............................. 356/328 |
| 7,301,625 B2 | 11/2007 | Brady et al. |
| 7,342,658 B2 | 3/2008 | Kowarz et al. |
| 7,692,784 B2* | 4/2010 | MacKinnon et al. .......... 356/300 |
| 2005/0185179 A1 | 8/2005 | Wang |

FOREIGN PATENT DOCUMENTS

| DE | 19533102 A1 | 3/1997 |
| WO | 0227285 A1 | 4/2002 |

OTHER PUBLICATIONS

Dudley et al : "Emerging Digital Micromirror Device 9DMD) Applications"; 2003 Society of Photo-Optical Instrumentation Engineers, Proceedings of SPIE, vol. 4985, 12 Page Document.

* cited by examiner

*Primary Examiner* — Layla Lauchman

(57) ABSTRACT

A device and method for optically examining the interior of turbid media including acts of spatially separating a plurality of wavelength bands contained in a broad-band light; separately modulating the plurality of wavelength bands; recombining the plurality of modulated wavelength bands to a beam of spectrally encoded broad-band light; illuminating a turbid medium with the beam of spectrally encoded broad-band light; detecting light emanating from the turbid medium with a detector and demodulating the detected light with a demodulator to provide spectroscopic information.

13 Claims, 5 Drawing Sheets

METHOD AND DEVICE FOR OPTICALLY EXAMINING THE INTERIOR OF TURBID MEDIA

FIELD OF INVENTION

The present invention relates to a method and to a device for optically examining the interior of turbid media.

BACKGROUND OF THE INVENTION

In the context of the present application, the term turbid medium is to be understood to mean a substance consisting of a material having a high light scattering coefficient, such as for example an intralipid solution or biological tissue. The term light is to be understood to mean non-ionizing electromagnetic radiation, in particular with wavelengths in the range between 400 nm and 1400 nm.

In the past decades, optics of turbid media such as biological tissue has become a widespread field of research and has found clinical applications in for instance monitoring (e.g. pulse oxymeter), cosmetics (e.g. port wine stain removal), and cancer treatment (e.g. photo dynamic therapy). Several techniques for optical imaging of turbid media (in particular for imaging biological tissue) are known, e.g. Optical Coherence Tomography, Confocal Microscopy; Two-Photon Microscopy, and Diffuse Optical Tomography. In diffuse optical imaging, a measurement geometry comprising many source and detector positions for acquisition of 3-D tomographic images is possible, or e.g. a geometry with limited numbers of sources and detectors (such as in a hand-held probe) to provide a simple map of the object to be imaged or to read-out just one or more specific parameters. In these applications, typically visible light, NIR (near infra-red), and/or IR (infra-red) light is used and this light can be provided as a continuous wave, in form of pulses, or as photon density waves, for example. Also, several different techniques using monochromatic light, multi-wavelength light, or a continuous spectrum are known in the art. Further tissue inherent fluorescence or fluorescence of a fluorescent contrast agent can be exploited. These applications all benefit in one way or another from the spectral features which are present in tissue, as will be explained with reference to FIG. 1.

Absorption spectra of the main chromophores which are present in, for instance, breast tissue are shown in FIG. 1. In FIG. 1 showing the respective absorptions of the main chromophores as a function of wavelength, it can be seen that absorption properties of the main chromophores hemoglobin, oxy-hemoglobin, water, and lipid differ considerably in their dependency on the wavelength of incident light. It can further be seen that the spectra of these constituents do not show features of narrow optical bandwidth but rather only features having a considerably large bandwidth.

Spectroscopy on tissue allows exploiting the different spectral characteristics such that the chromophores of the tissue and hence the composition of the tissue can be identified and, if desired, visualized and/or analyzed. Promising examples relying on in vivo optical spectroscopy of diffuse light emanating from tissue include imaging of breast cancer (e.g. by diffuse optical tomography), fluorescence imaging (e.g. using inherent fluorescence or fluorescent contrast agents) and monitoring of diabetes. However, an inherent problem occurring in spectroscopy on turbid media such as tissue is that, due to the relatively high amount of inherent scattering of light in tissue, the light emanating from the turbid medium under examination is strongly attenuated and, even more important, is of diffuse nature. Light, once diffusive, cannot be collimated effectively and hence acquisition of an optical spectrum of light emanating from such a turbid medium is inefficient. This inefficiency is a problem which has to be overcome to improve the applicability of tissue optics. The reason for this inefficiency will be described in the following.

For understanding the collection inefficiency occurring in optical examination of turbid media, a closer look on the optical characteristics is necessary. The "etendue" G which is also called acceptance, throughput, light-grasp, or collecting power is a property of an optical system which characterizes how "spread out" the light is in area and angle. The etendue can be defined in several equivalent ways. From the source point of view, it is the area A of the source times the solid angle Ω the system's entrance pupil subtends as seen from the source, i.e. $G = A\,\Omega$. This product is shown in FIG. 2. From the system point of view, the etendue is the area of the entrance pupil times the solid angle the source subtends as seen from the pupil. However, these definitions apply for infinitesimally small "elements" of area and solid angle and have to be summed over both the source and the diaphragm. A perfect optical system would produce an image with the same etendue as the source. In other words, in a perfect optical system, the etendue is conserved; in imperfect real systems however, the etendue usually gets worse (i.e. to higher values). The etendue is related to the Lagrange invariant and the Optical invariant.

In a system for optical examination of turbid media in which diffuse light is to be coupled into a spectrometer, the etendue (or collecting power) of the spectrometer is intrinsically much smaller than that of the diffuse source (which by its nature has an etendue close to the maximum possible). A conventional spectrometer relies on the narrow extent of a slit or pinhole to obtain sufficient spatial resolution on its detector, since the spatial resolution is subsequently translated into spectral resolution. Since the spectroscopy of diffuse light, as for example emanating from turbid media formed by biological tissue, is inherently inefficient due to the etendue mismatch described above, this seriously compromises detection threshold and sampling time. It has been found that this etendue problem can hardly be dealt with at the detector side. Making use of a large etendue detector would be preferable in view of the etendue mismatch. However, in conventional arrangements this is not possible in view of the required spectral resolution.

In principle, it would be advantageous to use a photo multiplier tube (PMT) as a detector in such devices since it is very sensitive (internal gain) and has a fast response (high bandwidth) combined with a large area (high etendue). However, using a photo multiplier tube (PMT) comes along with some problems such as a limited dynamic range and vulnerability to overexposure. Further, the sensitivity of a PMT drops significantly in the near infra-red (NIR) of the optical spectrum.

There are further constraints with respect to examination of living biological tissue. A white light source with high power and brightness is required to fulfill the maximum possible requirements with respect to measurement quality. If measurement time is an issue, a bright source is required. Extremely bright white light sources have become available based on supercontinuum generation using intense femtosecond light pulses propagating through a holey fiber. However, in biological tissue there is a so-called Maximum Permissible Exposure (MPE). For sub-second exposure in the near infra-red at small spot size, this can be in the order of one Watt.

Recently, a new type of spectrometer has been invented, the "Matrix Spectrometer" based on Coded Aperture Imaging. It uses a technique called Multimodal Multiplex Spectroscopy (MMS), which employs a wide area aperture with an encoded mask to increase the light throughput by an order of magnitude, given the same spectral resolution. U.S. Pat. No. 7,301,625 B2 shows an aperture coded spectrometer for spectral characterization of diffuse sources. The slit of conventional spectrometers is replaced by a spatial filter or mask. Using a number of different masks is proposed.

SUMMARY OF THE INVENTION

It is an object of the present invention to improve the light efficiency of spectroscopic examination of the interior of turbid media and to thereby improve the detection threshold and/or sampling time.

This object is solved by a method for optically examining the interior of turbid media according to claim 1. The method comprises the steps: providing broad-band light; spatially separating a plurality of wavelength bands contained in the broad-band light; separately modulating the plurality of wavelength bands; recombining the plurality of modulated wavelength bands to a beam of spectrally encoded broad-band light; illuminating a turbid medium with the beam of spectrally encoded broad-band light; detecting light emanating from the turbid medium with a detector and demodulating the detected light with a demodulator to provide spectroscopic information. Since the plurality of wavelength bands are separately modulated and thereafter recombined, spectroscopy on turbid media using large area and/or large acceptance angle detectors becomes possible. This increases the efficiency and allows for lower detection thresholds and/or shorter sampling times. Since broad-band light is used as an input, a relatively cheap white light source can be used for providing the light for illuminating the turbid medium. Thus, an overall cost reduction can be achieved.

According to one aspect, at least two wavelength bands have different widths with respect to wavelength.

Preferably, the plurality of wavelength bands is modulated such that at least two wavelength bands which are adjacent in the broad-band light are not adjacent with respect to a demodulation process in the demodulator. In this case, effects of cross-talk can be reliably suppressed. For example, two wavelength bands (channels) which are directly adjacent with respect to their wavelength ranges are modulated such that, with respect to the modulation scheme, the encoding of the channels by modulation is performed such that a detector/demodulator arrangement "sees" the channels at positions which are not adjacent to each other. As a result detected signals corresponding to the different channels can be reliably distinguished.

Preferably, the different wavelength bands of the plurality of wavelength bands are modulated such that for at least two adjacent wavelength bands the intensity detected by the detector is in the same order. In this case, crosstalk which could be caused if directly adjacent channels comprised large differences in intensity can be reliably prevented.

According to an aspect, the plurality of modulated wavelength bands is detected and analyzed before having illuminated the turbid medium; and the result is fed back to the step of modulating the plurality of wavelength bands. Thus, the spectrum of the collimated beam of spectrally encoded light can be adjusted depending on the result of the analysis. The distribution and intensity of channels can be adjusted to e.g. control that the collimated beam complies with the requirements of maximum permissible exposure (MPE).

Preferably, the demodulator provides a feedback to the step of modulating the plurality of wavelength bands. In this case, the spectrum of the collimated beam of spectrally encoded light can be adjusted depending on the information which is acquired after the beam has passed the turbid medium. Thus, specific spectral features of the turbid medium can be reliably resolved by appropriately adjusting the modulation process. Further, based on this information, the effects of crosstalk caused by the modulation process can be mitigated.

The object is further solved by a device for optically examining the interior of turbid media according to claim 7. The device comprises: a broad-band light source emitting a beam of broad-band light; a band separator spatially separating a plurality of wavelength bands contained in the broad-band light; a spatial light modulator separately modulating the plurality of wavelength bands; a light recombining unit recombining the plurality of modulated wavelength bands to a beam of spectrally encoded broad-band light; a measurement volume for illumination of a turbid medium with the beam of spectrally encoded broad-band light; a detector detecting light emanating from the measurement volume; and a demodulator demodulating the detected light to provide spectroscopic information. Since the plurality of wavelength bands are separately modulated and thereafter recombined, spectroscopy on turbid media using large area and/or large acceptance angle detectors is enabled. This increases the efficiency and allows for lower detection thresholds and/or shorter sampling times. Since the broad-band light is used to provide the light for illumination, a relatively cheap white light source can be used for providing the light for illuminating the turbid medium. Thus, an overall cost reduction can be achieved.

Preferably, an analyzing unit for analyzing the plurality of modulated wavelength bands before entering the measurement volume is provided which provides a feedback to the spatial light modulator. In this case, the beam of spectrally encoded broad-band light can be analyzed at a position before it impinges on the turbid medium. Thus, the distribution and intensity of different wavelength bands can be adapted for e.g. taking into account maximum permissible exposure (MPE).

If the demodulator provides a feedback to the spatial light modulator, the light modulation performed in the spatial light modulator can be adjusted depending on the signal acquired after the light has passed the turbid medium. Thus, the modulation can be adjusted such that optical features of the turbid medium can be reliably resolved.

If the detector is a photo multiplier tube, high sensitivity (internal gain), fast response (large bandwidth), and large area (high etendue) can all be realized. If a combination of the photo multiplier tube with a feedback loop is used, overexposure of the photo multiplier tube can be reliably prevented and the impinging radiation can be adapted to the dynamic range of the photo multiplier tube.

If the spatial light modulator comprises a micro-mirror device or a liquid crystal device, dynamical adjustments of the modulation can be easily achieved, in particular in combination with a feedback loop.

If the broad-band light source is adapted to emit polarized light, efficiency can be further improved (in particular in combination with a polarizing beam splitter), since more light can be sent to the turbid medium as compared to an implementation using non-polarized light and a normal beam splitter.

Preferably, the device is a medical optical examination device.

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

First Embodiment

Figure 3:
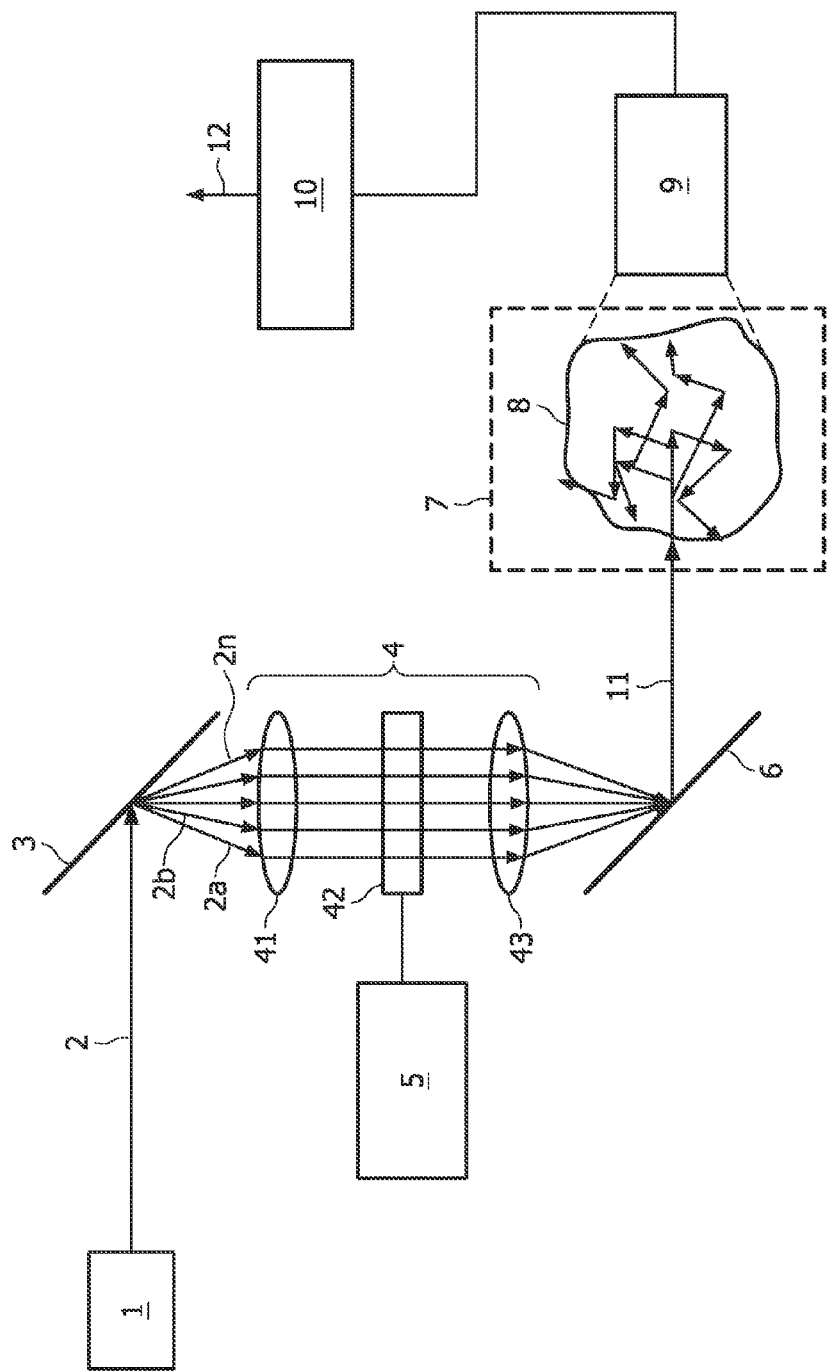
FIG. 3 schematically shows a first embodiment.

A first embodiment of the present invention will now be described with reference to FIG. 3. A device for examination of the interior of turbid media according to the first embodiment is formed by a spatial light modulation spectroscopy device. The device comprises a light source 1 emitting a collimated beam 2 of broad-band light, a band separator 3, a spatial light modulator 4, a light recombining unit 6, a measurement volume 7 for accommodating a turbid medium 8, a detector 9, and a demodulator 10.

The light source 1 is chosen such that white light with high power and brightness is emitted, i.e. the beam 2 comprises a continuous broad band of wavelengths covering a large plurality of wavelengths, preferably in the visible, IR, and/or NIR. The light source 1 may be pulsed. For example, the light source 1 is an extremely bright white light source based on super-continuum generation. For example, this is achieved by using intense femto-second light pulses propagating through a holey fiber. However, it is also possible to use a rather simple lamp emitting white light.

The collimated beam 2 of broad-band light is directed to the band separator 3. The band separator is adapted such that it spatially separates a plurality of wavelength bands ($2a$, $2b$, ..., $2n$) contained in the beam 2 of broad-band light. For example, the band separator 3 can be formed by a grating adapted for spatially splitting different bands of wavelengths contained in the beam 2 of broad-band light. It should be noted that the different bands of wavelengths neither need to have the same width with respect to wavelength range nor the same wavelength spacing with respect to each other (wavelength spacing).

The spatially separated wavelength bands ($2a$, ..., $2n$) are directed to the spatial light modulator (SLM) 4 for spatially modulating the separated wavelength bands in such a way that each of the wavelength bands ($2a$, ..., $2n$) receives a specific modulation. In the present embodiment, the spatial light modulator 4 is of the transmission-type. The spatial light modulator 4 comprises an input lens 41, a light modulating unit 42, an output lens 43, and a modulation source 5. The input lens 41 makes the respective beams of the distinct wavelength bands parallel. The light modulating unit 42 is connected to the modulation source 5 which controls the operation of the light modulating unit 42. The light modulating unit 42 can be mechanically realized, e.g. in form of a dedicated Nipkow-type disk or chopper or the like. Preferably, the light modulating unit 42 is formed by a micro-mirror device or a liquid crystal device.

Different ways of light modulation which are known in the art can be applied. For example frequency division multiplexing can be applied or time division multiplexing or both. The modulation scheme according to which modulation of the wavelength bands (channels) is performed is given by the light modulating unit 42 cooperating with the modulation source 5.

The independently modulated wavelength bands ($2a$, $2b$, ..., $2n$) are recombined to a collimated beam 11 of spectrally encoded broad-band light by a light recombining unit 6 which may e.g. be formed by another grating.

The collimated beam 11 of spectrally encoded broad-band light is used for illuminating a turbid medium 8 under examination which is accommodated in a measurement volume 7. Due to the turbid nature of the turbid medium 8 which can e.g. be formed by living biological tissue such as a female human breast, diffuse light emanates from the turbid medium in response to the illumination.

The diffuse light emanating from the illuminated turbid medium 8 is detected by the detector 9. The detector 9 is formed by a high-etendue photodetector comprising a large area and/or angle of acceptance. Suitable large-area high-NA detectors are photodiodes, APD arrays (avalanche photodiode arrays), and photo-multiplier tubes (PMT).

The signal detected by the detector 9 is decoded/demodulated by the demodulator 10 in order to restore the spectroscopic information contained in the diffuse light emanating from the turbid medium 8. Hence, the tissue-specific optical spectrum as imprinted by the turbid medium 8 on the emanated light is obtained. This obtained optical spectrum is then output by the demodulator 10 as an output signal 12.

It should be noted that, in the embodiment, the band separator 3, the light recombining unit 6, the lenses and the light modulating unit 42 are arranged in a so-called 4-f configuration.

Thus, according to the embodiment, a number of predefined wavelength bands (channels), which may have different width and or spacing, from a collimated white light source can each be coded in frequency and time domain using the band separator 3 and the spatial light modulator 4 (SLM). The wavelength bands are recombined to a single collimated beam 11 by a light recombining unit 6. The collimated and encoded beam 11 of possibly arbitrarily large optical bandwidth (white light) is used to illuminate the turbid medium 8 which can e.g. be formed by biological tissue. According to the embodiment, the diffuse light emanating from the turbid medium 8 is detected by a high-etendue photodetector (comprising a large area and/or angle of acceptance) followed by a demodulator such that the optical spectrum is obtained with high detection efficiency. Thus, spectrally coded light is advantageously combined with diffuse light spectroscopy and large area, high NA detectors such as photodiodes, avalanche photodiode arrays, or photo-multiplier tubes. The received signals are decoded/demodulated to restore the spectroscopic information and hence obtain the medium-specific optical spectrum as imprinted by the turbid medium on the light emanating from the turbid medium.

In principle, on the source side (i.e. in the light path before the turbid medium 8), crosstalk will be caused by spectral overlap and stray light in the spatial light modulator 4 and by electrical coupling and cross-modulation in the spatial light modulator 4 as well as in the associated driver electronics. Further, on the detector side, demodulation may cause additional crosstalk between spectral channels. Advantageously, the effect of crosstalk can be minimized by equalizing adjacent channels (which are likely to cause most of the crosstalk) on the detector. In the first embodiment, this can be achieved by appropriate selection of the channels with respect to band width and center position based e.g. on reference measurements or expected results. The modulation applied to a specific wavelength band (channel) in the spatial light modulator 4 can then be chosen to achieve the desired result. Further, based on such input information, channels (i.e. specific wavelength bands) which do not effectively contribute to the measurement result can be eliminated in the spatial light modulator 4. The latter is beneficial for the total light exposure on the tissue in applications to biological tissue as a turbid medium 8, since the optical power in the remaining channels can be increased without violating the MPE (maximum permissible exposure) limit.

It is further possible to operate the spatial light modulator 4 such that a quite complex modulation scheme is followed in which adjacent channels (wavelength bands) are not adjacent in the translated RF domain on the detection side. In this case, the relevant channels are independently modulated such that, for the demodulator 10 demodulating the signal corresponding to the detected diffuse light, these relevant channels are not located adjacent to each other.

Figure 2:
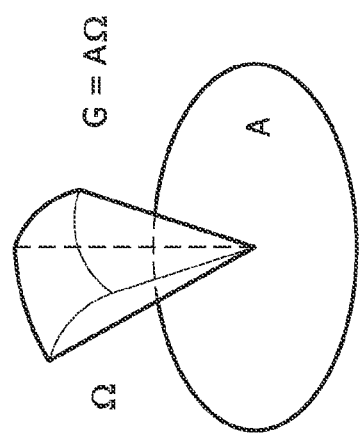
FIG. 2 is a drawing for explaining the etendue.
Figure 1:
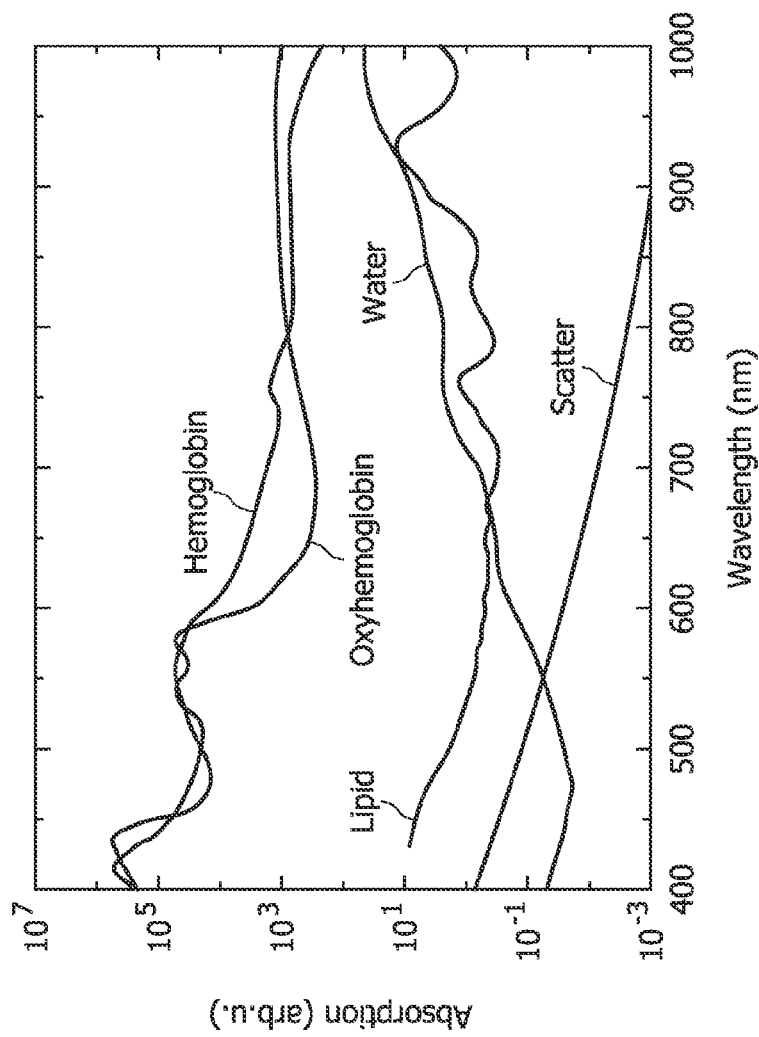
FIG. 1 schematically shows absorption spectra for different chromophores

The order and/or distribution of the wavelength bands may be changed between measurements and the joint results of the different measurements can be taken to identify and suppress effects of cross-talk. For example, an a priori known feature in the spectrum may mask another, more subtle but important feature in one configuration but not in another configuration of channel order and/or distribution. Thus, if the order and/or distribution of the wavelength bands are changed, the more subtle feature can be resolved. Since, as can be seen in FIG. 1, the spectral features in biological tissue do not show features smaller than a few nanometers in optical bandwidth, these results can be achieved with crosstalk and the number of channels both kept within reasonable limits.

The embodiment enables spectroscopy on highly scattering mediums using large area and/or large acceptance angle detectors. This increases the efficiency and allows for lower detection thresholds and/or shorter sampling times. The embodiment furthermore allows use of a rather cheap white light source and a relatively normal spectrometer on the front end (i.e. before the light is directed to the turbid medium) instead of an expensive light source (such as for instance multiple lasers) and an expensive spectrometer as in case of the prior art. The prior art requires such expensive components since, in the known implementation, a lot of light is lost because of the low acceptance area and/or narrow acceptance angle of the spectrometer which is located in the light path behind the turbid medium. Thus, according to the embodiment, overall cost reductions can be achieved.

Second Embodiment

Figure 4:
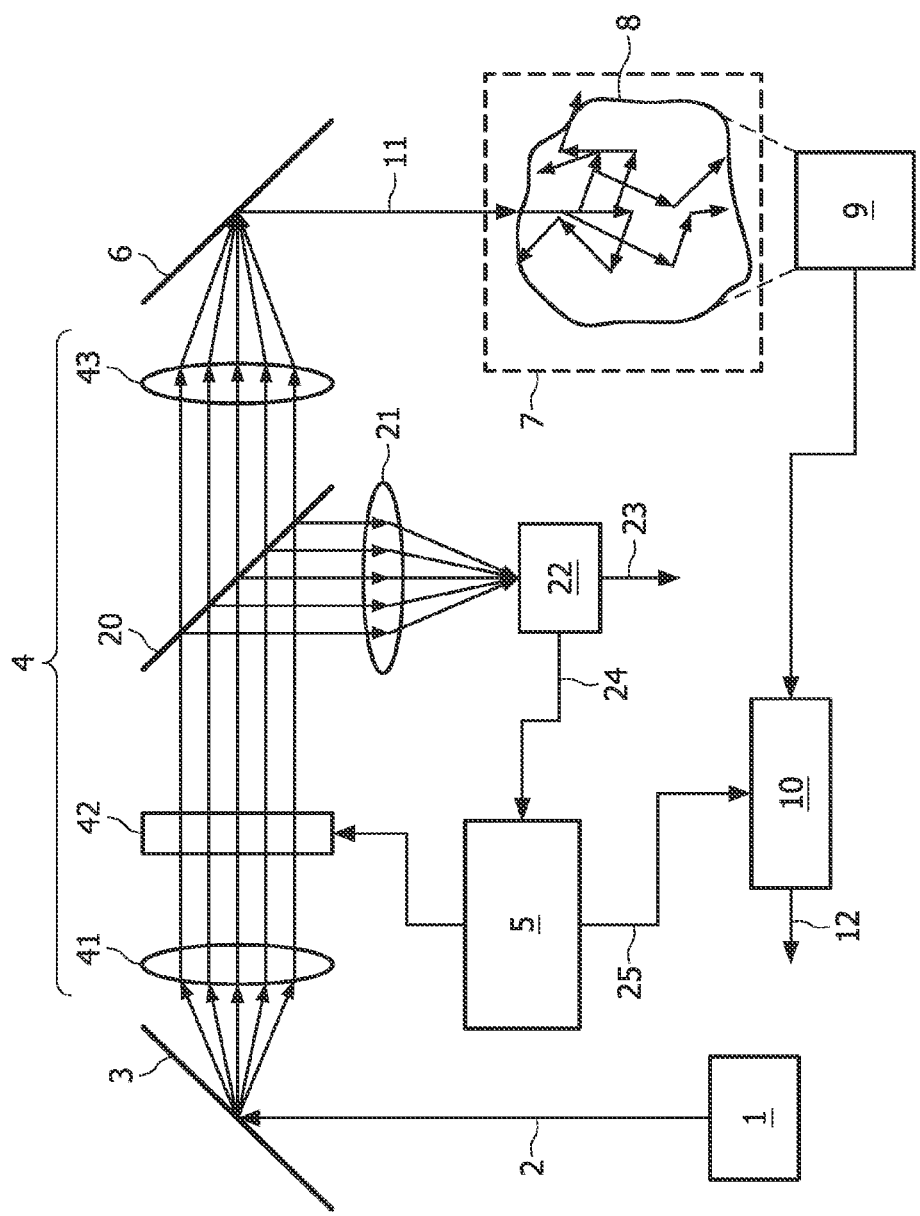
FIG. 4 schematically shows a second embodiment.

A second embodiment will now be described with respect to FIG. 4. The second embodiment substantially corresponds to the first embodiment but comprises additional features which will be described. Therefore, identical components are denoted by identical reference signs and their description will be omitted.

The second embodiment differs from the first embodiment in that a beam splitter 20 is introduced in the light path behind the light modulating unit 42. This beam splitter couples a portion of each of the plurality of modulated wavelength bands out and directs it, via a lens 21, to a light analyzing unit 22. The light analyzing unit 22 analyzes the light distribution in the plurality of modulated wavelength bands and outputs the results as an output signal 23. The light analyzing unit 22 can e.g. be formed by a spectrometer.

The light analyzing unit 22 is further coupled to the modulation source 5 of the spatial light modulator 4 to provide a feedback signal 24 to the modulation source 5. The modulation source 5 is further coupled to the demodulator 10 to provide a modulation signal 25 indicating the performed modulation. The modulation signal 25 allows the demodulator 10 to perform the appropriate demodulation operation.

Thus, in the second embodiment a feedback loop is realized. The feedback loop allows monitoring and altering the optical spectrum with which the turbid medium 8 is illuminated. The feedback loop operates in the following way: Via the beam splitter 20 and the light analyzing unit 22, the distribution and intensity of the different modulated wavelength bands is determined. The feedback signal 24 provides information about the result achieved by the light analyzing unit 22 to the modulation source 5. Based on this information, the modulation source 5 adapts the modulation to the different separated wavelength bands ($2a, \ldots, 2n$). The adaptation can be performed such that the optical spectrum with which the turbid medium is illuminated becomes equalized (with respect to the different channels) or becomes shaped in a specific way which is particularly suited for the turbid medium 8 under examination.

Further, the second embodiment achieves the advantages which have already been described with respect to the first embodiment.

Third Embodiment

A third embodiment will now be described with respect to FIG. 5. The third embodiment substantially corresponds to the second embodiment but comprises an additional feedback as will be described below. Again, identical components are denoted by identical reference signs and their description will be omitted.

Figure 5:
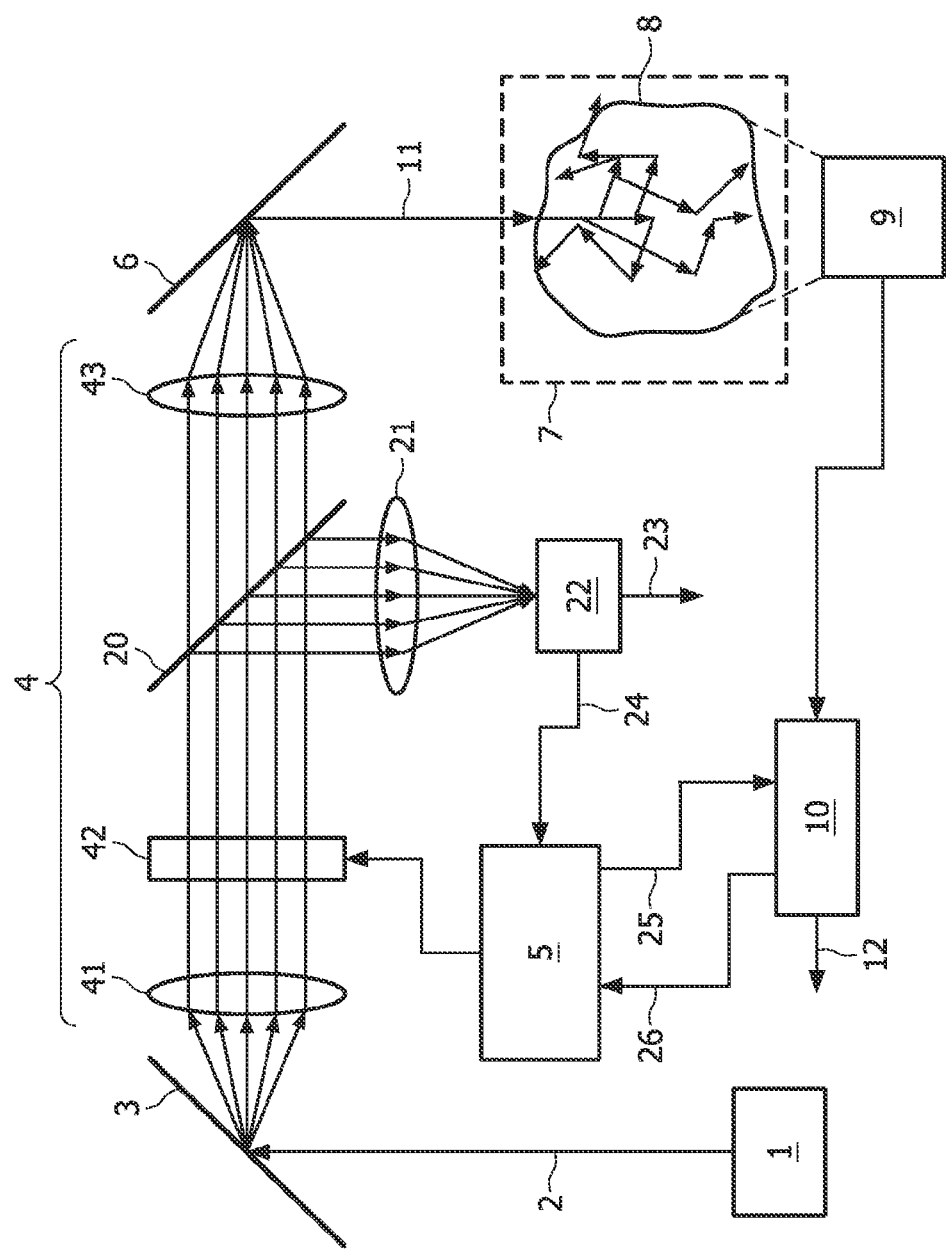
FIG. 5 schematically shows a third embodiment.

As can be seen in FIG. 5, an additional feedback loop from the detection side (behind the turbid medium) to the source side (upstream of the turbid medium) is provided. According to the shown example, the demodulator 10 outputs a feedback signal 26 which is provided to the modulation source 5 and thus to the spatial light modulator 4.

With this arrangement, further advantageous features can be realized. For example, the source spectrum, i.e. the spectrum of the spectrally encoded broad-band light which is used for illuminating the turbid medium 8, and the intensity of the different channels can be adaptively changed to the optimum probing spectrum based on the feedback information in the feedback signal 26. The changes can be performed depending on characteristics of the specific turbid medium 8 and on the MPE limit. Further, noise and crosstalk can be minimized by adaptively optimizing the spectral shape and the light intensity of the light used for irradiating the turbid medium 8.

It should be noted that the third embodiment also achieves the advantages which have been described with respect to the first and second embodiments.

Fourth Embodiment

Figure 6:
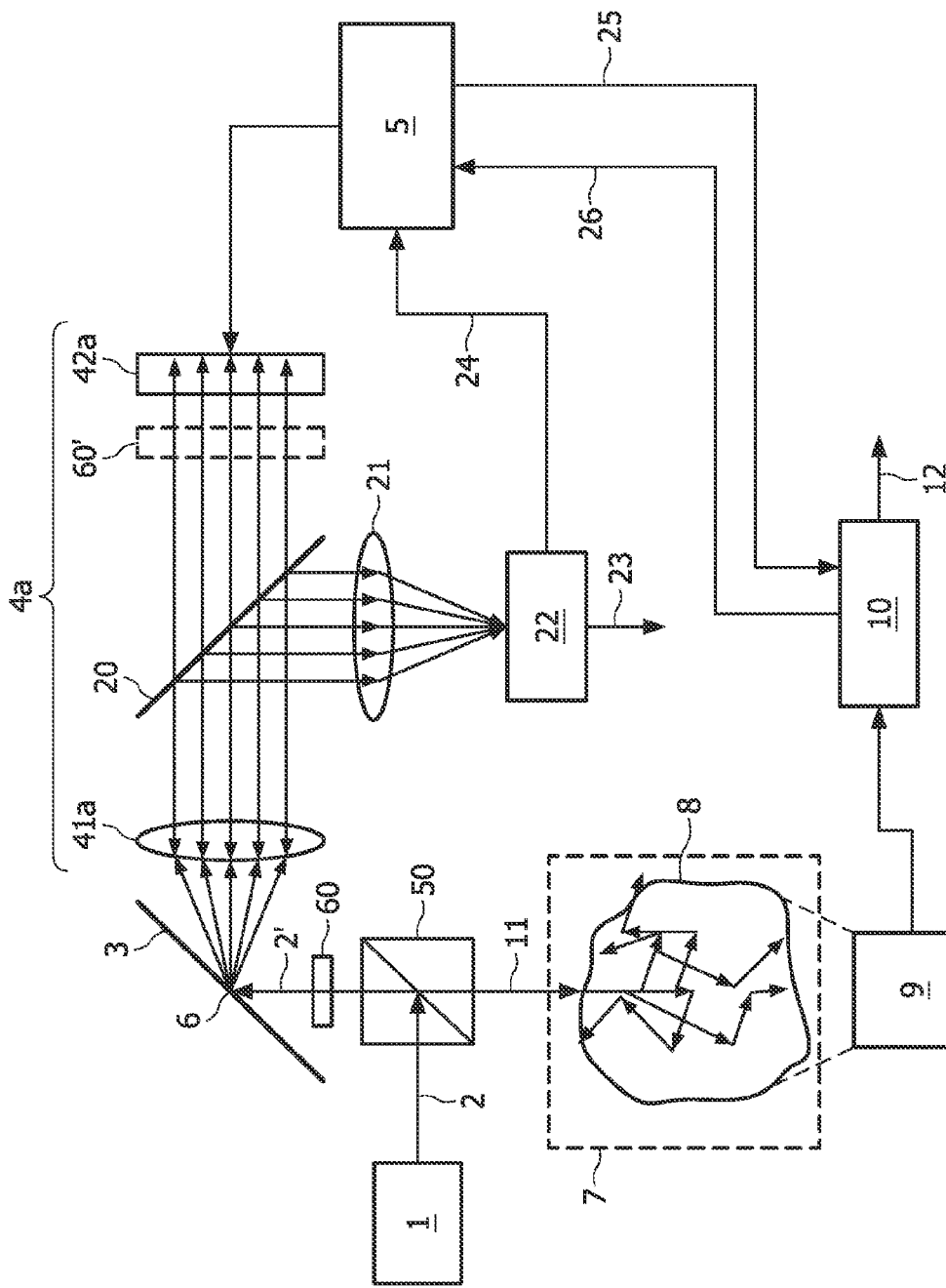
FIG. 6 schematically shows a fourth embodiment.

A fourth embodiment will now be described with respect to FIG. 6. The first to third embodiments described above all comprise a spatial light modulator 4 of the transmission type. The fourth embodiment differs from the third embodiment substantially in that a folded optics arrangement and a spatial light modulator 4a of the reflection type is used. Again, identical components are denoted by identical reference signs and their description will be omitted.

As can be seen in FIG. 1, the collimated beam 2 of broadband light from the light source 1 is directed to a beamsplitter 50 directing the beam to a band separator 3 which can e.g. be formed by a grating as in the first to third embodiments. In this embodiment as well, the band separator 3 separates a plurality of wavelength bands ($2a, 2b, \ldots, 2n$) contained in the beam 2 of broad-band light. The spatially separated wavelength bands ($2a, \ldots, 2n$) are directed to the spatial light modulator (SLM) 4a which comprises an input lens 41a and a light modulating unit 42a. However, in this embodiment, the light modulating unit 42a is of the reflection type, i.e. it comprise at least one reflective element and separately modulates the separated wavelength bands ($2a, \ldots, 2n$) as in the previous embodiments. Due to the reflection-type arrangement, the modulated wavelength bands are directed to the input lens 41a again which also acts as an output lens. The modulated wavelength bands are directed to the grating forming the spatial light separator 3 which also acts as a light recombining unit 6 in this embodiment. In this light recombining unit 6, the modulated wavelength bands (channels) are recombined to a collimated beam 11 of spectrally encoded broad-band light. This beam 11 passes the beamsplitter 50 and illuminates the turbid medium 8 under examination. The further features are similar to the third embodiment and thus will not be described again. In particular, the beam splitter 20 for coupling light to the light analyzing unit 22 is provided between the lens 41a and the light modulating unit 42a.

Preferably, in this embodiment a light source generating a linearly polarized beam, a polarizing beamsplitter 50, and a quarter-wave plate 60 are used in order to achieve efficient splitting of the input beam 2 and the (recombined) output beam. The output beam will be linearly polarized with orthogonal orientation to the input beam. When using a polarizing beam splitter and polarized light, more light can be sent to the turbid medium as compared to a configuration using a normal beam splitter and non-polarized light. Also, no feed back will occur to the input. Note that the quarter-wave plate 60 can be inserted before or after the grating or in front of the spatial light modulator (as indicated by 60' in FIG. 6). It may even be an integral part of the spatial light modulator. Each of these positions may be used, the choice amongst others depending on polarization properties of the other optical components in the light path.

The fourth embodiment substantially achieves the same advantages as the first to third embodiments. In particular, the feedback loops described with respect to the second and third embodiments are realized here as well. Due to the folded optics arrangement, however, a space-saving arrangement is allowed for.

It should be noted that the folded optics arrangement described with respect to the fourth embodiment as an alternative to the third embodiment is not restricted to this. As a skilled person will understand, the folded optics arrangement using a spatial light modulator of the reflection type can also be used in the first and second embodiments. Further, polarized light (making use of a light source emitting polarized light, a quarter-wave plate and a polarizing beam splitter) can be advantageously used in all embodiments that use a backfolded light path.

An example for the specification of a system comprising the 4-f configuration will now be given. For example, first the pixel size $\Delta x$ of the spatial light modulator is determined (e.g. $\Delta x=15$ µm for a typical, fast DMD with 20 kHz bandwidth). Next the wavelength interval $\Delta \lambda$ of a single channel that will pass such a pixel is determined (e.g. $\Delta \lambda=3$ nm). Next, the number of channels N or the maximum wavelength span is determined (e.g. N=100). The size of the spatial light modulator and the numerical aperture of the lens follow from these values. The required properties for the gratings (the band separator and the light recombining unit) follow once the other specifications have been determined. Then, the system losses have to be estimated and a source with appropriate wavelength span and output intensity has to be chosen. For example, a 5 mWatt/nm, single-mode fiber, bright source from Fianium supercontinuum laser with a wavelength range between 650 and 950 nm (with 800 nm center wavelength) seems particularly suitable.

In certain cases it would be beneficial to use a photo multiplier tube which combines a large photosensitive area (e.g. several square centimeters) with a high bandwidth (e.g. several hundreds of MHz) as a detector, since this would allow the use of photon density waves (PDW) in combination with the technique described in this specification.

With respect to the embodiments, it should be noted that both frequency division (for example several different source-modulated sinusoidally) and/or time division multiplexing can be applied. Further, a spread-spectrum radio technique can be applied.

It is possible to use shaping of the optical spectrum in order to optimize either spectral features or the maximum permissible exposure (MPE) of the turbid medium 8, or both, which is particularly relevant in medical applications on biological tissue. For example, the position and the width of the wavelength bands can be chosen such that the sensitivity to the specific spectral features of chromophores (cf. FIG. 1) is increased. In this context, it should be noted that the different wavelength bands ($2a, \ldots, 2n$) can have quite different widths or center distance.

Since the distinct wavelength bands are independently modulated, the spectral features which are adjacent in the optical spectrum, by choice do not have to be adjacent in the modulation spectrum. This can be advantageously used to fight occurrence of cross-talk.

The teaching of the embodiments can be combined with MMS (Multimodal Multiplex Spectroscopy) to, for example, improve cross-talk between wavelength bands. If the spatial light modulator 4 is a micro-mirror device or a liquid crystal device, dynamical adjustments are possible, possibly in combination with a feedback loop. The use of a feedback loop allows controlling the dynamic range of the system such that it is optimized and a photo multiplier tube (PMT) can be used as a detector. The feedback loop provides that overexposure of the PMT can be reliably prevented. As a consequence, the combination of using a PMT in combination with a feedback loop to control the light intensity allows achieving a high-bandwidth, high-etendue system of high sensitivity.

The invention claimed is:

1. A method for optically examining an interior of turbid media, the method comprising acts of:
   spatially separating, a plurality of wavelength bands of a broad-band light;
   separately modulating each of the plurality of wavelength bands, the modulating is controlled by a modulation source;
   recombining the plurality of modulated wavelength bands in a beam of spectrally encoded broad-band light to illuminate a turbid medium;
   receiving a signal corresponding to a light emanating from the turbid medium, and a signal from the modulation source authorizing demodulation;
   demodulating the detected light to provide spectroscopic information when authorized; and
   providing a first feedback directing the modulation source to adaptively change spectrum and intensity of the plurality of wavelength bands.

2. The method according to claim 1, wherein at least two of the plurality of wavelength bands have different widths with respect to wavelength.

3. The method according to claim 1, wherein the plurality of wavelength bands is modulated such that at least two wavelength bands which are adjacent in the broad-band light are not adjacent with respect to a demodulation process.

4. The method according to claim 1, wherein different wavelength bands of the plurality of wavelength bands are modulated such that for at least two adjacent wavelength bands the detected intensity is in the same order of magnitude.

5. The method according to claim 1, wherein the plurality of modulated wavelength bands is detected and analyzed before having illuminated the turbid medium, and the result is fed back for separately modulating the plurality of wavelength bands.

6. The method according to claim 1, further comprising an act of providing the spectroscopic information for separately.

7. A device for optically examining the interior of turbid media; the device comprising:
- a band separator configured to spatially separate a plurality of wavelength bands of a broad-band light;
- a spatial light modulator having a light modulating unit controlled by a modulation source and configured to separately modulate each of the plurality of wavelength bands;
- a light recombining unit configured to recombine the plurality of modulated wavelength bands in a beam of spectrally encoded broad-band light and illuminate a volume of a turbid medium;
- a demodulator configured to
  - receive a signal corresponding to light emanating from the volume and a signal from the modulation source authorizing demodulation,
  - demodulate the detected light to provide spectroscopic information when authorized, and
  - provide a first feedback directing the modulation source adaptively change spectrum and intensity of the plurality of wavelength bands.

8. The device according to claim 7, further comprising an analyzing unit configured to
- analyze the plurality of modulated wavelength bands; and
- provide a second feedback.

9. The device according to claim 7, wherein the changes directed by the first feedback minimize noise and crosstalk and depend on characteristics of the turbid medium and on a maximum permissible exposure limit.

10. The device according to claim 7, wherein the detector is a photo multiplier tube.

11. The device according to claim 7, wherein the spatial light modulator comprises a micro-mirror device or a liquid crystal device or a chopper or Nipkow disk.

12. The device according to claim 7, further comprising a broad-band light source configured to emit polarized broad-band light.

13. The device according to claim 7, wherein the device is a medical optical examination device.

* * * * *